(12) United States Patent
Albert et al.

(10) Patent No.: US 9,951,091 B2
(45) Date of Patent: Apr. 24, 2018

(54) PROCESS FOR PREPARING TRIS[3-(ALKOXYSILYL)PROPYL] ISOCYANURATES

(71) Applicant: Evonik Degussa GmbH, Essen (DE)

(72) Inventors: Philipp Albert, Rheinfelden (DE); Eckhard Just, Rheinfelden (DE)

(73) Assignee: EVONIK DEGUSSA GmbH, Essen (DE)

( * ) Notice: Subject to any disclaimer, the term of this patent is extended or adjusted under 35 U.S.C. 154(b) by 0 days.

(21) Appl. No.: 15/658,074

(22) Filed: Jul. 24, 2017

(65) Prior Publication Data

US 2018/0022762 A1 Jan. 25, 2018

(30) Foreign Application Priority Data

Jul. 22, 2016 (EP) .................................. 16180821

(51) Int. Cl.
C07D 251/34 (2006.01)
C07F 7/18 (2006.01)

(52) U.S. Cl.
CPC .......... C07F 7/1876 (2013.01); C07D 251/34 (2013.01)

(58) Field of Classification Search
CPC .................................................. C07D 251/34
USPC ........................................................ 544/221
See application file for complete search history.

(56) References Cited

U.S. PATENT DOCUMENTS 3,220,972 A * 11/1965 Lamoreaux .......... B01J 31/2226
502/169
3,494,951 A 2/1970 Berger 3,517,001 A * 6/1970 Berger .................. C07F 7/0892
156/329
5,986,124 A * 11/1999 Tachikawa ............ C07F 7/1876
556/479
2012/0149901 A1* 6/2012 Tsuchida ............... C07F 7/0879
544/221

FOREIGN PATENT DOCUMENTS

GB          1 202 498 A        8/1970

OTHER PUBLICATIONS

Extended European Search Report dated Jan. 16, 2017 in Patent Application No. 16180821.7 (with English translation of categories of cited documents).
Norio Yoshino, et al., "Synthesis of bone formation deriving biosilanes", Colloids and Surfaces . B. Biointerfaces. Elsevier, vol. 66, Nr. 1, XP22939862, 2008, pp. 71-76.
U.S. Appl. No. 09/329,371, filed Feb. 20, 2001, 6,191,297, Batz-Sohn, Christoph; Karch, Ralf; Prinz, Matthias; Seebald, Steffen.
U.S. Appl. No. 09/818,997, filed Mar. 28, 2001, 2002/0008011, Batz-Sohn, Christoph; Sonnenschein, Raymund.

* cited by examiner

*Primary Examiner* — Venkataraman Balasubramanian
(74) *Attorney, Agent, or Firm* — Grüneberg and Myers PLLC

(57) ABSTRACT

A tris[3-(alkoxysilyl)propyl] isocyanurate from the group of tris[3-(trialkoxysilyl)propyl] isocyanurate, tris[3-(alkyldialkoxysilyl)propyl] isocyanurate and tris[3-(dialkylalkoxysilyl)propyl] isocyanurate is prepared by hydrosilylation, by a) initially charging a mixture of at least one hydroalkoxysilane from the group of hydrotrialkoxysilane, hydroalkyldialkoxysilane, hydrodialkylalkoxysilane [called H-silane(s) for short] and a Pt catalyst, b) heating the mixture to a temperature of 40 to 170° C., c) then adding or metering in 1,3,5-triallyl-1,3,5-triazine-2,4,6(1H,3H,5H)-trione, at least one carboxylic acid and at least one alcohol as cocatalyst while mixing, and d) leaving the mixture to react and then working up the product mixture thus obtained.

14 Claims, No Drawings

PROCESS FOR PREPARING TRIS[3-(ALKOXYSILYL)PROPYL] ISOCYANURATES

BACKGROUND OF THE INVENTION

Field of the Invention

The present invention relates to a particularly economically viable process for preparing tris[3-(trialkoxysilyl)propyl] isocyanurate, tris[3-(alkyldialkoxysilyl)propyl] isocyanurate and tris[3-(dialkylalkoxysilyl)propyl] isocyanurate (also referred to collectively hereinafter as tris[3-(alkoxysilyl)propyl] isocyanurates for short), wherein 1,3,5-triallyl-1,3,5-triazine-2,4,6(1H,3H,5H)-trione is hydrosilylated with a hydrotrialkoxysilane, hydroalkyldialkoxysilane or hydrodialkylalkoxysilane in the presence of a Pt catalyst, a carboxylic acid and a further cocatalyst.

Description of the Related Art

Tris[3-(alkoxysilyl)propyl] isocyanurates are silanes that can be used as crosslinkers. By virtue of the three alkoxysilyl groups, of which each alkoxysilyl group after hydrolysis can enter into one, two or three chemical bonds, three up to nine chemical bonds are theoretically possible. By virtue of these significant crosslinking opportunities, tris[3-(alkoxysilyl)propyl] isocyanurates are of interest for various applications. A further advantage of tris[3-(alkoxysilyl)propyl] isocyanurates is the high thermal stability that enables use in the high-temperature range. Tris[3-(alkoxysilyl)propyl] isocyanurates can therefore be used advantageously as crosslinker, for example, in paint and rubber formulations and as adhesion promoter in paints and adhesives in a wide variety of different industries. The high crosslinking density additionally allows production of scratch-resistant coatings and barrier layers.

JP4266400B describes the preparation of an aromatic silane compound by hydrosilylation of an aromatic vinyl compound. The catalyst used is a platinum complex in the presence of a carboxylic acid.

U.S. Pat. No. 5,986,124 relates to a process for preparing a silane compound by hydrosilylation of a carbon double bond by means of a trialkoxyhydrosilane in the presence of a platinum catalyst and a carboxylic acid. Through the use of platinum catalysts together with carboxylic acids, it is possible to achieve a conversion of about 80% in the hydrosilylation, but crude products thus obtained still include a considerable proportion of impurities and/or by-products.

EP 0587462 describes a composition composed of an unsaturated polyorganosiloxane, an organohydropolysiloxane, an acid, a platinum compound and additives, wherein the components are emulsified in water and used for surface release treatment. The crosslinking is effected via hydrosilylation in the course of heating.

EP 0856517 discloses a process for hydrosilylation of an unsaturated compound in the presence of a metal compound of transition groups 8 to 10 of the Periodic Table of the Elements. The hydrosilylation is conducted in the presence of an accelerator.

EP 1869058/WO 2006/113182 presents a process for preparing tris[3-(trialkoxysilyl)propyl] isocyanurate. The preparation proceeds via the cracking of silyl organocarbamate in the presence of a catalytic amount of a carboxylate salt.

EP 0583581 teaches the preparation of a silyl organocarbamate from an aminosilane. The silyl organocarbamate is subsequently converted to the silyl isocyanurate in the presence of a "cracking catalyst".

EP 1885731 discloses a process for preparing isocyanatosilanes and silyl isocyanurate. The synthesis starts with a silyl organocarbamate. By catalytic cracking, the isocyanatosilane is released, and the conversion of the isocyanatosilane to the silyl isocyanurate is effected in a trimerization reaction zone.

CA 943544 describes the preparation of a silyl organoisocyanurate from a haloalkylsilane and a metal cyanate in the presence of a solvent. The solvent and the salt formed are removed after the reaction.

U.S. Pat. No. 3,607,901 relates to the preparation of isocyanatosilanes and isocyanuratosilanes proceeding from chloroalkyltrialkoxysilanes and a metal cyanate.

U.S. Pat. No. 3,517,001 teaches, inter alia, the preparation of 1,3,5-tris(trimethoxysilylpropyl) isocyanurate by hydrosilylation of 1,3,5-tris(allyl isocyanurates) with trimethoxysilane in the presence of hexachloroplatinic acid. The yield is reported as 40%.

U.S. Pat. No. 3,821,218 describes the preparation of 1,3,5-tris(trimethoxysilylpropyl) isocyanurate proceeding from chloropropyltrimethoxysilane and potassium cyanate in DMF as solvent.

US 2013/0158281 discloses a process for hydrosilylation of an unsaturated compound with a silyl hydride. The catalysts used are Fe complexes, Ni complexes, Mn complexes or Co complexes.

CN 101805366 describes the preparation of 1,3,5-tris (trimethoxysilylpropyl) isocyanurate by cyclocondensation of isocyanatopropyltrimethoxysilane.

CS 195549 relates to the hydrosilylation of vinylcyclohexane with hydrosilanes. In example 4, vinylcyclohexane is hydrolysed by means of triethoxysilane in the presence of platinic acid and trifluoroacetic acid.

SUMMARY OF THE INVENTION

The problem addressed by the present invention was that of providing a process for preparing tris[3-(alkoxysilyl) propyl] isocyanurates, i.e. from the group of tris[3-(trialkoxysilyl)propyl] isocyanurate, tris[3-(alkyldialkoxysilyl)propyl] isocyanurate and tris[3-(dialkylalkoxysilyl)propyl] isocyanurate, where alkyl is especially—but not exclusively—methyl or ethyl and alkoxy is methoxy or ethoxy, in which a Pt catalyst is used in conjunction with a carboxylic acid and the disadvantages detailed above are reduced if possible via a controlled reaction regime, specific feed ratios and/or further additions. Furthermore, another aim was, if possible, to conduct the process with a minimum concentration of costly platinum and without the separate addition of an aliphatic or aromatic solvent and to increase the yield of target product. It was also desirable to keep the content of carboxylic acid remaining in the target product to a minimum.

It has been found that, surprisingly, significantly better yields of target product, i.e. a tris[3-(alkoxysilyl)propyl] isocyanurate, are achieved when the hydrosilylation is performed by initially charging the hydroalkoxysilane together with a Pt catalyst, heating the initially charged mixture and then, while mixing, metering 1,3,5-triallyl-1,3,5-triazine-2, 4,6(1H,3H,5H)-trione as olefin component into the initial charge together with a carboxylic acid and leaving them to react over a defined period of time, wherein, preferably, a defined amount of a further co-catalyst is added to the 1,3,5-triallyl-1,3,5-triazine-2,4,6(1H,3H,5H)-trione/carboxylic acid mixture in the form of at least one alcohol, preferably a C1-C10 alcohol, for example—but not exclusively—from the group of benzyl alcohol, diglycol monomethyl ether, tert-butanol, ethanol and/or methanol, and so the reaction and the selectivity and hence the yield of the hydrosilylation is markedly promoted.

It has been found here to be particularly advantageous that the present process is preferably conducted with a homogeneous platinum(0) complex catalyst, especially a "Karstedt catalyst", a Speyer catalyst, hexachloroplatinum(IV) acid or a supported, i.e. heterogeneous, Pt catalyst, for example Pt on activated carbon. In addition, a "Karstedt catalyst" is preferably used in the form of a platinum(0) complex catalyst solution, especially dissolved in xylene or toluene. The present procedure also makes it possible to reduce the content of Pt catalyst/the Pt loss, and hence to save costly Pt. Moreover, it has been found to be particularly advantageous in the present process to use a carboxylic acid from the group of benzoic acid, 3,5-di-tert-butylbenzoic acid, 3,5-di-tert-butyl-4-hydroxybenzoic acid, propionic acid and/or acetic acid.

DETAILED DESCRIPTION OF THE INVENTION

A product mixture obtained by the present process is suitably worked up by distillation, optionally under reduced pressure, and the desired (target) product is obtained.

In the case of use of a heterogeneous catalyst, the latter can suitably be separated from the product mixture prior to the distillation, for example by filtration or centrifugation, and this Pt catalyst thus recovered can advantageously be recycled into the process.

For instance, the target product is obtained as bottom product in the distillation conducted after the reaction and, if necessary, after the removal of a heterogeneous catalyst; the target product is not distilled over in the distillative workup and is obtained as a colourless bottom product. Furthermore, the process described can already be conducted in an economically viable manner at a comparatively low temperature of 40-60° C.

In the present process, the double bonds of the olefin component used here can advantageously be virtually completely hydrosilylated, advantageously giving rise to only a very low level of by-products.

Furthermore, the present process, i.e. that according to the invention, can advantageously be conducted without separate addition of an aliphatic or aromatic hydrocarbon as solvent or diluent, and with only a small proportion of the carboxylic acid (co-)catalyst component which remains in the target product.

The present invention thus provides a process for preparing a tris[3-(alkoxysilyl)propyl] isocyanurate from the group of tris[3-(trialkoxysilyl)propyl] isocyanurate, tris[3-(alkyldialkoxysilyl)propyl] isocyanurate and tris[3-(dialkylalkoxysilyl)propyl] isocyanurate by hydrosilylation, by
  initially charging a mixture of at least one hydroalkoxysilane from the group of hydrotrialkoxysilane, hydroalkyldialkoxysilane, hydrodialkylalkoxysilane [called H-silane(s) for short] and a Pt catalyst,
  heating the mixture to a temperature of 40 to 170° C.,
  then adding or metering in 1,3,5-triallyl-1,3,5-triazine-2,4,6(1H,3H,5H)-trione, at least one carboxylic acid and at least one alcohol while mixing, preferably a mixture comprising 1,3,5-triallyl-1,3,5-triazine-2,4,6(1H,3H,5H)-trione, at least one carboxylic acid and at least one alcohol, as cocatalyst,
  leaving the mixture to react and then working up the product mixture thus obtained.

In the process according to the invention, H-silane is advantageously used relative to olefin component in a molar ratio of 1:0.1 to 0.5, preferably of 1:0.2 to 0.4, especially—to give just a few of the possible intermediate values here that will be clear or derivable for the person skilled in the art from the figures above and the present figures, in a representative manner and by way of example—1:0.13, 1:0.15, 1:0.18, 1:0.23, 1:0.25, 1:0.28, 1:0.3, 1:0.33, 1:0.35, 1:0.38.

The H-silane used here is preferably hydrotrimethoxysilane (TMOS), hydrotriethoxysilane (TEOS), methyldiethoxysilane (DEMS), methyldimethoxysilane (DMMS), dimethylethoxysilane (DMES) and/or dimethylmethoxysilane (MDMS).

Moreover, in the process according to the invention, the olefin component used is 1,3,5-triallyl-1,3,5-triazine-2,4,6(1H,3H,5H)-trione.

Advantageously, in the process according to the invention, it is preferable to use H-silane relative to alcohol in a molar ratio of 1:0.01 to 0.2, preferably 1:0.02 to 0.18, more preferably 1:0.03 to 0.15, even more preferably 1:0.04 to 0.1, especially 1:0.05 to 0.06. Preferably, for this purpose, at least one alcohol is selected from the group of the C1-C10 alcohols, more preferably at least one from the group of tert-butanol, ethanol, methanol, benzyl alcohol and diglycol monomethyl ether.

Moreover, in the process according to the invention, H-silane is advantageously used relative to Pt in a molar ratio of $1:1\times10^{-4}$ to $1\times10^{-9}$, preferably $1:1\times10^{-5}$ to $1\times10^{-8}$, especially of $1:1\times10^{-5}$ to $9\times10^{-6}$.

The Pt catalyst used here is suitably a heterogeneous Pt catalyst, preferably Pt applied to a solid catalyst support, especially Pt on activated carbon, or a homogeneous Pt catalyst, preferably a Pt complex catalyst, such as hexachloroplatinum(IV) acid, also called "Speyer catalyst", especially hexachloroplatinum(IV) acid dissolved in acetone, preferably a Pt(0) complex catalyst, more preferably a "Karstedt catalyst", even more preferably a platinum(0)-1,3-divinyl-1,1,3,3-tetramethyldisiloxane complex, especially a "Karstedt catalyst" in xylene or toluene with a Pt(0) content of 0.5% to 5% by weight. Such a solution generally contains a platinum(0)-1,3-divinyl-1,1,3,3-tetramethyldisiloxane complex dissolved in xylene or toluene, and a solution used in accordance with the invention is advantageously used in dilute form and preferably contains a Pt content of 0.5% to 5% by weight. Thus, in the process according to the invention, it is advantageous to use a Pt catalyst from the group of "Karstedt catalyst", especially a "Karstedt catalyst" solution, preferably platinum(0)-1,3-divinyl-1,1,3,3-tetramethyldisiloxane complex in xylene or toluene with a Pt(0) content of 0.5% to 5% by weight, hexachloroplatinum(IV) acid, preferably "Speyer catalyst", especially hexachloroplatinum(IV) acid dissolved in acetone, or Pt supported on activated carbon.

Further, in the process according to the invention, H-silane is preferably used relative to carboxylic acid in a molar ratio of $1:1\times10^{-3}$ to $30\times10^{-3}$, more preferably $1:1\times10^{-3}$ to $10\times10^{-3}$, especially of $1:2\times10^{-3}$ to $6\times10^{-3}$.

For this purpose, the carboxylic acid is preferably selected from the group of benzoic acid, 3,5-di-tert-butylbenzoic acid, 3,5-di-tert-butyl-4-hydroxybenzoic acid, propionic acid, acetic acid.

Preferably, the process according to the invention is performed by
initially charging and heating the H-silane and Pt catalyst components as a mixture,
combining olefin component, carboxylic acid and alcohol and metering the mixture comprising olefin component [1,3,5-triallyl-1,3,5-triazine-2,4,6(1H,3H,5H)-trione], carboxylic acid and alcohol into the initial charge at a temperature in the initial charge of 40-135° C. while mixing over a period of time of 1 to 10 hours and
subsequently leaving the mixture to react over a period of time of 0.5 to 2 hours, the reaction preferably being conducted under protective gas, especially under nitrogen; it is optionally possible—if a heterogeneous catalyst is used—to remove it from the product mixture thus obtained,
performing the subsequent distillative workup of the product mixture obtained preferably at 45-150° C. and a reduced pressure, by removing especially low boilers that are present, for example xylene/toluene, alcohol, carboxylic acid, excess H-silane and optionally olefin component, from the product mixture to obtain the (target) product.

It is thus possible, in general, to execute the process according to the invention—with all its possible combinations of the features detailed in the present description—as follows:

For the performance of the hydrosilylation according to the invention for preparation of a tris[3-(alkoxysilyl)propyl] isocyanurate, the hydroalkoxysilane (H-silane), preferably trimethoxysilane (TMOS), triethoxysilane (TEOS-H), methyldiethoxysilane (DEMS), methyldimethoxysilane (DMMS), dimethylethoxysilane (DMES) or dimethylmethoxysilane (MDMS), is initially charged together with a platinum catalyst, suitably a "Speyer catalyst", preferably hexachloroplatinum(IV) acid in acetone or hexachloroplatinum(IV) acid hexahydrate dissolved in acetone or a "Karstedt catalyst", the latter preferably being used in the form of a platinum(0) complex catalyst solution, or Pt on activated carbon, in a stirred reactor with metering apparatus, heating/cooling apparatus, reflux apparatus and distillation apparatus, suitably under protective gas, for example nitrogen, and the initially charged mixture is heated to a temperature of 40 to 170° C. Subsequently, while mixing, 1,3,5-triallyl-1,3,5-triazine-2,4,6(1H,3H,5H)-trione as olefin component, at least one carboxylic acid, preferably benzoic acid, 3,5-di-tert-butylbenzoic acid, 3,5-di-tert-butyl-4-hydroxybenzoic acid and/or acetic acid, and at least one alcohol, for example one of the aforementioned C1-C10 alcohols, is added or metered in as a further so-called co-catalyst. The olefin, carboxylic acid and alcohol components can be added or metered into the hydroalkoxysilane/platinum catalyst mixture of the initial charge here in portions or continuously, and individually and successively or advantageously in the form of a 1,3,5-triallyl-1,3,5-triazine-2,4,6(1H,3H,5H)-trione/carboxylic acid/alcohol mixture over a defined period of time, preferably under temperature control and over 1 to 10 or more hours, where the metering time may clearly be dependent on the batch size and the reactor design, and the reaction mixture or product mixture is left to react further, preferably while mixing and under temperature control, suitably at a temperature of 60-100° C., especially over 0.5 to 2 hours. Thus, in present processes, the respective feedstocks are preferably used in a well-defined molar ratio:

H-silane to olefin component in a molar ratio of 1:0.1 to 0.5

H-silane to alcohol in a molar ratio of 1:0.01 to 0.2
H-silane to Pt in a molar ratio of $1:1\times10^4$ to $1\times10^{-9}$
H-silane to carboxylic acid in a molar ratio of $1:1\times10^{-3}$ to $30\times10^{-3}$ In addition, the "Karstedt catalyst" solution used is preferably prepared from a conventional "Karstedt catalyst" concentrate (platinum(0)-1,3-divinyl-1,1,3,3-tetramethyldisiloxane complex, platinum content: 20.37% by weight) (also called "Karstedt concentrate" for short), the concentrate preferably being adjusted to a Pt content of 0.5% to 5% by weight by the addition of xylene or toluene.

A product mixture thus obtained is a suitably worked up by distillation to obtain the desired (target) product. For this purpose, the distillation is preferably conducted commencing at 45° C. to 150° C. and a reduced pressure (vacuum distillation at less than 1 bar and falling, especially not more than 0.1 bar), wherein low boilers that are present in particular, for example carboxylic acid, alcohol, excess H-silane and any olefin component still present are removed from the product mixture. If a heterogeneous Pt catalyst is used for the performance of the process according to the invention, the heterogeneous Pt catalyst can be separated from the product mixture obtained after the reaction in the course of the product workup, i.e. prior to the distillation step, for example by filtration or centrifugation, and advantageously be recycled back into the process.

It is thus advantageously possible in accordance with the invention to obtain tris[3-(alkoxysilyl)propyl] isocyanurates in comparatively high yield and selectivity, i.e. with only small proportions of by-products, even on the industrial scale in a simple and economically viable manner.

The examples which follow provide additional illustration of the present invention without restricting the subject-matter:

EXAMPLES

Analytical Methods:
NMR Measurements:
Instrument: Bruker
Frequency: 500.1 MHz ($^1$H NMR)
Scans: 32
Temperature: 303 K
Solvent: $CDCl_3$
Standard: 0.5% TMS (tetramethylsilane)

Explanations are given below with regard to naming of target product and by-products formed in the synthesis with respect to the present $^1$H NMR evaluations using the example of the structural formula of a tris[3-(trialkoxysilyl)propyl] isocyanurate. The determinations of selectivities with respect to tris[3-(methyldialkoxysilyl)propyl] isocyanurate and tris[3-(dimethylalkoxysilyl)propyl] isocyanurate were conducted analogously and are listed in the tables for Examples 6 and 7.

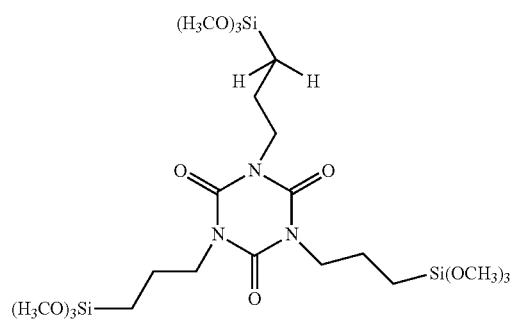

In the target product: functional group S1 (Si—CH$_2$—)

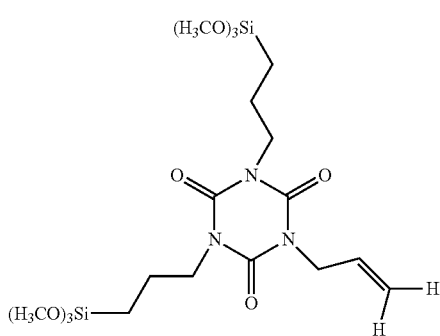

in the so-called allyl derivative: functional group A1

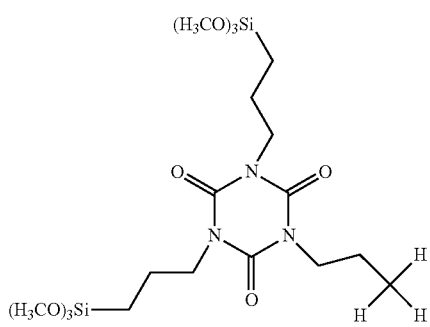

in the so-called propyl derivative: functional group P1

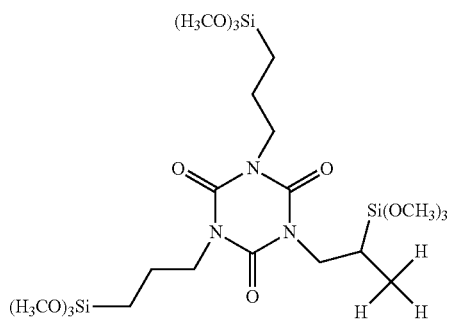

in the so-called isopropyl derivative: functional group I1

The experiments were evaluated using the product formed in the hydrosilylation of the 1,3,5-triallyl-1,3,5-triazine-2,4,6(1H,3H,5H)-trione. The more allylic double bonds were converted to the target product and the fewer secondary components were formed, the better the product quality and the performance/selectivity of the catalyst system. A high selectivity is very important because the secondary components can be removed by distillation from the target product only with a very high level of complexity, if at all.

The 1H NMR spectra were evaluated using the hydrogen atoms included in the structural formula drawings. The hydrosilylation gives rise to Si—$CH_2$— groups that are characteristic of the target product. The Si—$CH_2$— groups were identified with S1, the allylic groups ($C=CH_2$— group) with A1, the propyl group ($C_3H_7$— group) with P1 and the isopropyl group with I1. The evaluation of the 1H NMR spectra and the calculation of the functional groups was shown after each experiment in the tables. The evaluated signals from the $^1H$ NMR form triplets (t) for the S1 and P1 group, double doublets (dd) for the A1 group, and doublets (d) for the I1 group.

Chemicals Used:

"Karstedt concentrate" (platinum(0) 1,3-divinyl-1,1,3,3-tetramethyldisiloxane complex, platinum content: 20.37% by weight), HERAEUS Acetone, pure, LABC Labortechnik Hexachloroplatinum(IV) acid hexahydrate, platinum content 40% by weight, HERAEUS Platinum-activated carbon, hydrogenation catalyst, platinum content 10% by weight, MERCK Benzyl alcohol, puriss, SIGMA ALDRICH Diethylene glycol monomethyl ether >98% by weight, MERCK Xylene Technical, VWR Chemicals Dynasylan® TMOS (trimethoxysilane), EVONIK Industries Dynasylan® TEOS-H (triethoxysilane), EVONIK Industries Dynasylan® DEMS (methyldiethoxysilane), EVONIK Industries Dynasylan® DMES (dimethylethoxysilane), EVONIK Industries TIACROS® (1,3,5-triallyl-1,3,5-triazine-2,4,6(1H,3H,5H)-trione), EVONIK Industries Benzoic acid ≥99.5% by weight, ROTH 3,5-Di-tert-butylbenzoic acid >98.0% by weight, TOKYO CHEMICAL INDUSTRY 3,5-Di-tert-butyl-4-hydroxybenzoic acid, >98.0% by weight, TOKYO CHEMICAL INDUSTRY Acetic acid, ≥99% by weight, SIGMA-ALDRICH Methanol ≥99.5% by weight, MERCK Ethanol ≥99.8% by weight, ROTH tert-Butanol, ≥99.0% by weight (for synthesis), ROTH Chloroform-d1 ($CDCl_3$)+0.5% by weight of TMS, DEUTERO Benzene-d6, DEUTERO Tetramethylsilane, DEUTERO Preparation of "Karstedt-Catalyst" No. 1 with Platinum Content 2% by Weight in Xylene In a 0.2 l glass bottle, 9.8 g of "Karstedt concentrate" (platinum(0) 1,3-divinyl-1,1,3,3-tetramethyldisiloxane complex, platinum content 20.37%) were mixed with 90.2 g of xylene.

Preparation of "Karstedt-Catalyst" No. 2 with Platinum Content 2% by Weight in Toluene In a 0.2 l glass bottle, 9.8 g of "Karstedt concentrate" (platinum(0) 1,3-divinyl-1,1,3,3-tetramethyldisiloxane complex, platinum content 20.37% by weight) were mixed with 90.2 g of toluene.

Preparation of "Karstedt-Catalyst" No. 3 with Platinum Content 0.4% by Weight

In a 0.1 l glass bottle, 196.4 mg of "Karstedt concentrate" (platinum(0) 1,3-divinyl-1,1,3,3-tetramethyldisiloxane complex, platinum content 20.37% by weight) were mixed with 9.8 g of toluene.

Preparation of Catalyst 4 from Hexachloroplatinum(IV) Acid Hexahydrate Solution in Acetone with Pt Content 2.34% by Weight In a 12 l plastic vessel, 530 g of $H_2PtCl_6 \times 6H_2O$ were dissolved in 9.8 l of acetone. The catalyst solution thus prepared was used after maturing for 8 weeks.

Having generally described this invention, a further understanding can be obtained by reference to certain specific examples which are provided herein for purposes of illustration only, and are not intended to be limiting unless otherwise specified.

Comment on the Comparative Examples which Follow:

The synthesis in ampoules described in U.S. Pat. No. 5,986,124 cannot be conducted on the industrial scale. In order that the experiments can be better compared with the inventive examples, the experiments were conducted in a stirred tank or flask. Furthermore, in the examples in U.S. Pat. No. 5,986,124, different unsaturated compounds were used, and so a direct comparison with the present invention would not be possible; thus, TAICROS® was used in the comparative examples which follow.

Comparative Example 1: (Based on Example 1 from U.S. Pat. No. 5,986,124)

0.2003 mol (24.5 g) of Dynasylan® TMOS, 0.1 ml of Catalyst No. 1, a further 40.0 g of toluene as additional solvent/diluent, 0.0665 mol (16.6 g) of TAICROS® and 0.4 ml of acetic acid were initially charged in a 0.25 l stirred apparatus with jacketed coil condenser and stirred in an oil bath heated to 53-55° C. for 2.5 hours. This gave 79.9 g of incompletely converted and colourless bottom product. The volatile components were not removed.

Evaluation of the $^1H$ NMR spectrum with regard to Comparative Example 1:

| Solvent: CDCl$_3$ + 0.5% TMS | Signal at [ppm] | Integral I | N Number of protons | I/N | % (mol) |
|---|---|---|---|---|---|
| S1 | 0.66 | 100.00 | 2 | 50.00 | 73.8 |
| A1 | 5.25 | 34.79 | 2 | 17.40 | 25.7 |
| P1 | 0.94 | 0.61 | 3 | 0.20 | 0.3 |
| I1 | 1.01 | 0.43 | 3 | 0.14 | 0.2 |

Result: 45.8% of the allyl groups were converted by hydrosilylation to trimethoxysilylalkyl groups (cf. S1). 53.7% of the allyl groups (A1) have not been converted, and 0.3% propyl groups (P1) and 0.2% isopropyl groups (I1) that contaminate the product have formed. The reaction is incomplete.

Comparative Example 2: (Based on Example 1 from U.S. Pat. No. 5,986,124)

0.2003 mol (32.9 g) of Dynasylan® TEOS-H, 0.1 ml of Catalyst No. 3, a further 40.0 g of toluene as additional solvent/diluent, 0.0665 mol (16.6 g) of TAICROS® and 0.4 ml of acetic acid were initially charged in a 0.251 stirred apparatus with reflux condenser and stirred in an oil bath heated to 50-57° C. for 2.5 hours. This gave 88.2 g of incompletely converted and colourless bottom product. The volatile components were not removed.

Evaluation of the $^1H$ NMR Spectrum with Regard to Comparative Example 2:

| Solvent: CDCl$_3$ + 0.5% TMS | Signal at [ppm] | Integral I | N Number of protons | I/N | % (mol) |
|---|---|---|---|---|---|
| S1 | 0.64 | 100.00 | 2 | 50.00 | 86.2 |
| A1 | 5.26 | 14.59 | 2 | 7.30 | 12.6 |
| P1 | 0.94 | 0.33 | 3 | 0.33 | 0.6 |
| I1 | 1.06 | 0.35 | 3 | 0.35 | 0.6 |

Result: 86.2% of the allyl groups were converted by hydrosilylation to trimethoxysilylalkyl groups (cf. S1). 12.6% of the allyl groups (A1) have not been converted, and 0.6% propyl groups (P1) and 0.6% isopropyl groups (I1) that contaminate the product have formed. The reaction is incomplete.

Comparative Example 3: (with Acetic Acid Only, No Addition of Alcohol)

1.2 mol of DYNASYLAN® TMOS and 0.2 g of Catalyst No. 1 (corresponding to 0.0205 mmol of Pt) were initially charged in a 0.5 l stirred apparatus with reflux condenser, metering apparatus. At a temperature of 76-91° C., a mixture consisting of 0.33 mol of TAICROS® and 6.77 mmol of acetic acid was metered in within 1 h. Thereafter, the mixture was left to react further at about 87-92° C. for about 1 further hour. Subsequently, 55.0 g of low boilers were removed at 90-120° C. and a pressure of <0.1 mbar. This gave 170.7 g of incompletely converted, colourless bottom product.

Evaluation of the $^1H$ NMR Spectrum with Regard to Comparative Example 3:

| Solvent: CDCl$_3$ + 0.5% TMS | Signal at [ppm] | Integral I | N Number of protons | I/N | % (mol) |
|---|---|---|---|---|---|
| S1 | 0.66 | 100.00 | 2 | 50.00 | 73.8 |
| A1 | 5.25 | 34.79 | 2 | 17.40 | 25.7 |
| P1 | 0.94 | 0.61 | 3 | 0.20 | 0.3 |
| I1 | 1.01 | 0.43 | 3 | 0.14 | 0.2 |

Result: 73.8% of the allyl groups were converted by hydrosilylation to trimethoxysilylalkyl groups (cf. S1). 25.7% of the allyl groups (A1) have not been converted, and 0.3% propyl groups (P1) and 0.2% isopropyl groups (I1) that contaminate the product have formed. The reaction is incomplete.

Comparative Example 4

1.2 mol of Dynasylan® TMOS, 0.2 g of "Karstedt catalyst" (corresponding to 0.0205 mmol of Pt), 34.38 mmol of methanol and 6.55 mmol of benzoic acid were initially charged in a 0.5 l stirred apparatus with reflux condenser, metering apparatus. At a temperature of 73-82° C., 0.33 mol of TAICROS® was metered in within 1 hour. Thereafter, the mixture was left to react further at 81° C. for another 1 hour. Subsequently, 89.5 g of low boilers were removed at 35-127° C. and a pressure of <0.1 mbar. This gave 134.2 g of incompletely converted and colourless bottom product.

Evaluation of the $^1$H NMR Spectrum from Comparative Example 4:

| Solvent: CDCl$_3$ + 0.5% TMS | Signal at [ppm] | Integral | N Number of protons | I/N | % (mol) |
|---|---|---|---|---|---|
| S1 | 0.66 | 100.00 | 2 | 50.00 | 42.5 |
| A1 | 5.25 | 134.10 | 2 | 67.05 | 57.0 |
| P1 | 0.94 | 1.24 | 3 | 0.41 | 0.4 |
| I1 | 1.01 | 0.36 | 3 | 0.12 | 0.1 |

Result: 42.5% of the allyl groups were converted by hydrosilylation with TMOS to trimethoxysilylalkyl groups (cf. S1). 57.0% of the allyl groups (A1) were not converted. 0.4% propyl groups (P1) and 0.1% isopropyl groups (I1) that contaminate the product were formed. The conversion of the allyl groups is incomplete, and only a low level of by-products is formed.

Comparative Example 5

1.2 mol of Dynasylan® TMOS, 0.2 g of "Karstedt catalyst" (corresponding to 0.0205 mmol of Pt) and 34.38 mmol of methanol were initially charged in a 0.5 l stirred apparatus with reflux condenser, metering apparatus. At a temperature of 70-87° C., a mixture consisting of 0.33 mol of TAICROS® and 6.55 mmol of benzoic acid was metered in within 1 hour. Thereafter, the mixture was left to react further at 81° C. for another 1 hour. Subsequently, 41.5 g of low boilers were removed at 61-121° C. and a pressure of <0.1 mbar. This gave 183.0 g of incompletely converted and colourless bottom product.

| Evaluation of the 1H NMR spectrum from Comparative Example 5: Solvent: CDCl$_3$ + 0.5% TMS | Signal at [ppm] | Integral | N Number of protons | I/N | % (mol) |
|---|---|---|---|---|---|
| S1 | 0.66 | 100.0 | 2 | 50.00 | 81.5 |
| A1 | 5.25 | 21.75 | 2 | 10.87 | 17.7 |
| P1 | 0.94 | 1.09 | 3 | 0.36 | 0.6 |
| I1 | 1.01 | 0.38 | 3 | 0.13 | 0.2 |

Result: 81.5% of the allyl groups were converted by hydrosilylation with TMOS to trimethoxysilylalkyl groups (cf. 51). 17.7% of the allyl groups (A1) were not converted. 0.6% propyl groups (P1) and 0.2% isopropyl groups (I1) that contaminate the product were formed. The conversion of the allyl groups is incomplete, and only a low level of by-products is formed.

Comparative Example 6

0.33 mol (83.1 g) of TAICROS®, 0.2 g of Catalyst No. 1 (corresponding to 0.0205 mmol of Pt) and 6.79 mmol (1.7 g) of 3,5-di-tert-butyl-4-hydroxybenzoic acid were initially charged in a 0.5 l stirred apparatus with reflux condenser, metering apparatus. At a temperature of 91-111° C., 1.2 mol (146.6 g) of Dynasylan® TMOS were supposed to be metered in. The hydrosilylation is highly exothermic and, after metered addition of 18 g of Dynasylan® TMOS, the temperature had already risen from 91 to 97° C. within 9 minutes. Once a further 72 g of Dynasylan® TMOS had been metered in within 27 minutes and the temperature had risen to 108° C., it was not possible to detect any exothermicity in the course of further addition of Dynasylan® TMOS. The reaction mixture cooled down from 108 to 89° C. within a few minutes. The experiment was therefore stopped after metered addition of a total of 90 g of Dynasylan® TMOS; in other words, the reaction had stopped and the conversion in this procedure thus remained correspondingly incomplete. 68 g of Dynasylan® TMOS were not metered in.

Note:

The present comparative experiments for preparation of tris[3-(alkoxysilyl)propyl] isocyanurates by hydrosilylation of 1,3,5-triallyl-1,3,5-triazine-2,4,6(1H,3H,5H)-trione (TAICROS®) in the presence of a Pt catalyst system composed of Pt catalyst and carboxylic acid show that a comparatively low conversion of the double bond of well below 90 mol % is discovered when a mixture of H-silane, Pt catalyst, carboxylic acid and TAICROS® is used, heated and reacted as such H-silane and Pt catalyst are initially charged and heated and a mixture of TAICROS® and carboxylic acid is metered in H-silane, Pt catalyst and alcohol are initially charged and heated and a mixture of TAICROS® and carboxylic acid is metered in H-silane, Pt catalyst, carboxylic acid and alcohol are initially charged and heated and TAICROS® is metered in or TAICROS®, Pt catalyst and carboxylic acid are initially charged and heated and H-silane is metered in.

Example 1

1.2 mol of Dynasylan® TMOS and 0.2 g of Catalyst No. 1 (corresponding to 0.0205 mmol of Pt) were initially charged in a 0.5 l stirred apparatus with reflux condenser, metering apparatus. At a temperature of 74-92° C., a mixture consisting of 0.33 mol of TAICROS®, 6.55 mmol of benzoic acid and 34.38 mmol of methanol was metered in within 1 hour. Thereafter, the mixture was left to react further at about 84-96° C. for about 1 further hour. Subsequently, 22.4 g of low boilers were removed at 83-119° C. and a pressure of <0.1 mbar. This gave 203.5 g of completely converted and colourless bottom product.

Evaluation of the $^1$H NMR Spectrum with Regard to Inventive Example 1:

| Solvent: CDCl$_3$ + 0.5% TMS | Signal at [ppm] | Integral I | N Number of protons | I/N | % (mol) |
|---|---|---|---|---|---|
| S1 | 0.66 | 100.00 | 2 | 50.00 | 98.6 |
| A1 | 5.25 | 0.01 | 2 | 0.01 | <0.1 |
| P1 | 0.94 | 1.72 | 3 | 0.57 | 1.1 |
| I1 | 1.01 | 0.38 | 3 | 0.13 | 0.3 |

Result: 98.6% of the allyl groups were converted by hydrosilylation to trimethoxysilylalkyl groups (cf. S1). Allyl groups (A1) are no longer detectable. 1.1% propyl groups (P1) and 0.3% isopropyl groups (I1) that contaminate the product were formed. The conversion of the allyl groups is complete, and only a low level of by-products is formed.

Example 2

1.2 mol of Dynasylan® TMOS and 0.2 g of Catalyst No. 1 (corresponding to 0.0205 mmol of Pt) were initially charged in a 0.5 l stirred apparatus with reflux condenser, metering apparatus. At a temperature of 62-88° C., a mixture consisting of 0.33 mol of TAICROS®, 6.55 mmol of benzoic acid and 33.73 mmol of tert-butanol was metered in within 1 hour. Thereafter, the mixture was left to react further at about 79-88° C. for about 1 further hour. Subsequently, 20.5 g of low boilers were removed at 104-118° C. and a pressure of <0.1 mbar. This gave 204.4 g of completely converted and colourless bottom product.

Evaluation of the $^1$H NMR Spectrum with Regard to Inventive Example 2:

| Solvent: CDCl$_3$ + 0.5% TMS | Signal at [ppm] | Integral I | N Number of protons | I/N | % (mol) |
|---|---|---|---|---|---|
| S1 | 0.66 | 100.00 | 2 | 50.00 | 98.5 |
| A1 | 5.26 | 0.05 | 2 | 0.03 | <0.1 |
| P1 | 0.94 | 1.77 | 3 | 0.59 | 1.2 |
| I1 | 1.01 | 0.40 | 3 | 0.13 | 0.3 |

Result: 98.5% of the allyl groups were converted by hydrosilylation to trimethoxysilylalkyl groups (cf. S1). Allyl groups (A1) are no longer detectable. 1.2% propyl groups (P1) and 0.3% isopropyl groups (I1) that contaminate the product were formed. The conversion of the allyl groups is complete, and only a low level of by-products is formed.

Example 3

1.2 mol of Dynasylan® TMOS and 0.2 g of Catalyst No. 1 (corresponding to 0.0205 mmol of Pt) were initially charged in a 0.5 l stirred apparatus with reflux condenser, metering apparatus. At a temperature of 72-90° C., a mixture consisting of 0.33 mol of TAICROS®, 6.66 mmol of acetic acid and 34.38 mmol of methanol was metered in within 1 hour. Thereafter, the mixture was left to react further at about 78-88° C. for about 1 further hour. Subsequently, 20.0 g of low boilers were removed at 83-123° C. and a pressure of <0.1 mbar. This gave 202.9 g of completely converted and colourless bottom product.

Evaluation of the $^1$H NMR Spectrum with Regard to Inventive Example 3:

| Solvent: CDCl$_3$ + 0.5% TMS | Signal at [ppm] | Integral I | N Number of protons | I/N | % (mol) |
|---|---|---|---|---|---|
| S1 | 0.66 | 100.00 | 2 | 50.00 | 98.6 |
| A1 | 5.25 | 0.23 | 2 | 0.12 | 0.2 |
| P1 | 0.94 | 1.45 | 3 | 0.48 | 1.0 |
| I1 | 1.01 | 0.36 | 3 | 0.12 | 0.2 |

Result: 98.6% of the allyl groups were converted by hydrosilylation to trimethoxysilylalkyl groups (cf. S1). Allyl groups (A1) are still detectable in very small amounts. 1.0% propyl groups (P1) and 0.2% isopropyl groups (I1) that contaminate the product were formed. The conversion of the allyl groups is complete, and only a low level of by-products is formed.

Example 4

3.5 mol of Dynasylan® TEOS-H and 0.6 g of Catalyst No. 1 (corresponding to 0.0615 mmol of Pt) were initially charged in a 1 l stirred apparatus with reflux condenser, metering apparatus. At a temperature of 67-97° C., a mixture consisting of 0.973 mol of TAICROS®, 18.83 mmol of benzoic acid and 102.02 mmol of ethanol was metered in within 2 hours. Thereafter, the mixture was left to react further at about 97-103° C. for about 1 further hour. Subsequently, 100.6 g of low boilers were removed at about up to 140° C. and a pressure of <0.1 mbar. This gave 721.2 g of completely converted and colourless bottom product.

Evaluation of the $^1$H NMR Spectrum with Regard to Inventive Example 4:

| Solvent: CDCl$_3$ + 0.5% TMS | Signal at [ppm] | Integral I | N Number of protons | I/N | % (mol) |
|---|---|---|---|---|---|
| S1 | 0.64 | 100.00 | 2 | 50.00 | 98.2 |
| A1 | 5.26 | — | 2 | — | <0.1 |
| P1 | 0.94 | 2.10 | 3 | 0.70 | 1.4 |
| I1 | 1.06 | 0.63 | 3 | 0.21 | 0.4 |

Result: 98.2% of the allyl groups were converted by hydrosilylation to triethoxysilylalkyl groups (cf. S1). Allyl groups (A1) are no longer detectable. 1.4% propyl groups (P1) and 0.4% isopropyl groups (I1) that contaminate the product were formed. The conversion of the allyl groups is complete, and only a low level of by-products is formed.

Example 5

3.5 mol of Dynasylan® TEOS-H and 0.6 g of Catalyst No. 1 (corresponding to 0.0615 mmol of Pt) were initially charged in a 1 l stirred apparatus with reflux condenser, metering apparatus. At a temperature of 70-99° C., a mixture consisting of 0.973 mol of TAICROS®, 19.98 mmol of acetic acid and 102.02 mmol of ethanol was metered in within 2 hours. Thereafter, the mixture was left to react further at about 90-101° C. for about 1 further hour. Subsequently, 98.4 g of low boilers were removed at 48-145° C. and a pressure of <0.1 mbar. This gave 719.6 g of completely converted and colourless bottom product.

Evaluation of the $^1$H NMR Spectrum with Regard to Inventive Example 5:

| Solvent: CDCl$_3$ + 0.5% TMS | Signal at [ppm] | Integral | N Number of protons | I/N | % (mol) |
|---|---|---|---|---|---|
| S1 | 0.64 | 100.00 | 2 | 50.00 | 98.7 |
| A1 | 5.26 | — | 2 | — | <0.1 |
| P1 | 0.94 | 1.50 | 3 | 0.50 | 1.0 |
| I1 | 1.06 | 0.45 | 3 | 0.15 | 0.3 |

Result: 98.7% of the allyl groups were converted by hydrosilylation to triethoxysilylalkyl groups (cf. S1). Allyl groups (A1) are no longer detectable. 1.0% propyl groups (P1) and 0.3% isopropyl groups (I1) that contaminate the product were formed. The conversion of the allyl groups is complete, and only a low level of by-products is formed.

Example 6

0.60 mol of Dynasylan® DEMS (methyldiethoxysilane) and 0.1 g of Catalyst No. 1 (corresponding to 0.01025 mmol of Pt) were initially charged in a 0.25 l stirred apparatus with reflux condenser, metering apparatus. At a temperature of 89-125° C., a mixture consisting of 0.167 mol of TAICROS®, 1.64 mmol of benzoic acid and 32.6 mmol of ethanol was metered in within 1.5 hours. Thereafter, the mixture was left to react further at about 110° C. for about 1 further hour. Subsequently, 12.6 g of low boilers were removed at 65-112° C. and a pressure of <0.1 mbar. This gave 108.4 g of completely converted and colourless bottom product. As well as the target product, the following trace impurities were evaluated via the $^1$H NMR spectra:

Evaluation of the $^1$H NMR Spectrum with Regard to Inventive Example 6:

| Solvent: $C_6D_6$ + 0.5% TMS | Signal at [ppm] | Integral | N Number of protons | I/N | % (mol) |
|---|---|---|---|---|---|
| S1 | 0.62 | 100.00 | 2 | 50.00 | 97.9 |
| A1 | 5.25 | — | 2 | — | <0.1 |
| P1 | 0.75 | 2.33 | 3 | 0.78 | 1.5 |
| I1 | 0.87 | 0.85 | 3 | 0.28 | 0.6 |

Result: 97.9% of the allyl groups were converted by hydrosilylation to methyldiethoxysilylalkyl groups (cf. S1). Allyl groups (A1) are no longer detectable. 1.5% propyl groups (P1) and 0.6% isopropyl groups (I1) that contaminate the product were formed. The conversion of the allyl groups is complete, and only a low level of by-products is formed.

Example 7

0.60 mol of Dynasylan® DMES (dimethylethoxysilane) and 0.1 g of Catalyst No. 1 (corresponding to 0.01025 mmol of Pt) were initially charged in a 0.25 l stirred apparatus with reflux condenser, metering apparatus. At a temperature of 56-83° C., a mixture consisting of 0.167 mol of TAICROS®, 1.64 mmol of benzoic acid and 32.6 mmol of ethanol was metered in within 1 hour. Thereafter, the mixture was left to react further at about 88-93° C. for about 1 further hour. Subsequently, 8.8 g of low boilers were removed at 75-124° C. and a pressure of <0.1 mbar. This gave 95.0 g of completely converted and colourless bottom product.

Evaluation of the $^1$H NMR Spectrum with Regard to Inventive Example 7:

| Solvent: $C_6D_6$ + 0.5% TMS | Signal at [ppm] | Integral | N Number of protons | I/N | % (mol) |
|---|---|---|---|---|---|
| S1 | 0.54 | 100.00 | 2 | 50.00 | 99.6 |
| A1 | 5.25 | — | 2 | — | <0.1 |
| P1 | 0.75 | 0.03 | 3 | 0.01 | <0.1 |
| I1 | 0.87 | 0.57 | 3 | 0.19 | 0.4 |

Result: 99.6% of the allyl groups were converted by hydrosilylation to dimethylethoxysilylalkyl groups (cf. S1). Allyl groups (A1) and propyl groups (P1) are undetectable. 0.4% isopropyl groups (I1) that contaminate the product were formed. The conversion of the allyl groups is complete, and only a low level of by-products is formed.

Example 8

30.0 mol of Dynasylan® TMOS and 2.4 g of Catalyst No. 1 (corresponding to 0.246 mmol of Pt) were initially charged in an 8l stirred apparatus with reflux condenser, metering apparatus. At a temperature of 74-80° C., a mixture consisting of 9.36 mol of TAICROS®, 184 mmol of benzoic acid and 978 mmol of methanol was metered in within 2¾ hours. Thereafter, the mixture was left to react further at 80° C. for about 1 further hour. Subsequently, 264.7 g of low boilers were removed at 140° C. and a pressure of <0.1 mbar. This gave 5735 g of completely converted and colourless bottom product.

Evaluation of the $^1$H NMR Spectrum with Regard to Inventive Example 8:

| Solvent: $C_6D_6$ + 0.5% TMS | Signal at [ppm] | Integral I | N Number of protons | I/N | % (mol) |
|---|---|---|---|---|---|
| S1 | 0.66 | 100.0 | 2 | 50.00 | 98.5 |
| A1 | 5.25 | 0.05 | 2 | 0.03 | <0.1 |
| P1 | 0.94 | 1.83 | 3 | 0.61 | 1.2 |
| I1 | 1.01 | 0.43 | 3 | 0.14 | 0.3 |

Result: 98.5% of the allyl groups were converted by hydrosilylation to trimethoxysilylalkyl groups (cf. S1). Allyl groups (A1) are still detectable only in very small amounts. 1.2% propyl groups (P1) and 0.2% isopropyl groups (I1) that contaminate the product were formed. The conversion of the allyl groups is complete, and only a low level of by-products is formed.

Example 9

1.2 mol of Dynasylan® TMOS and 0.2 g of Catalyst No. 1 (corresponding to 0.0205 mmol of Pt) were initially charged in a 0.5 l stirred apparatus with reflux condenser, metering apparatus. At a temperature of 45-47° C., a mixture consisting of 0.33 mol of TAICROS®, 6.55 mmol of benzoic acid and 34.38 mmol of methanol was metered in within 2¾ hours. Thereafter, the mixture was left to react further for another 2¼ hours, in the course of which the reaction mixture had gradually risen exothermically to 108° C. Subsequently, 23.3 g of low boilers were removed at 48-131° C. and a pressure of <0.1 mbar. This gave 205.3 g of completely converted and colourless bottom product.

Evaluation of the $^1$H NMR Spectrum with Regard to Inventive Example 9:

| Solvent: $CDCl_3$ + 0.5% TMS | Signal at [ppm] | Integral | N Number of protons | I/N | % (mol) |
|---|---|---|---|---|---|
| S1 | 0.64 | 100.0 | 2 | 50.00 | 97.9 |
| A1 | 5.26 | — | 2 | — | <0.1 |
| P1 | 0.94 | 1.89 | 3 | 0.63 | 1.2 |
| I1 | 1.06 | 1.34 | 3 | 0.45 | 0.9 |

Result: 97.9% of the allyl groups were converted by hydrosilylation with TMOS to trimethoxysilylalkyl groups (cf. S1). Allyl groups (A1) are no longer detectable. 1.2% propyl groups (P1) and 0.9% isopropyl groups (I1) that contaminate the product were formed. The conversion of the allyl groups is complete, and only a low level of by-products is formed.

Example 10

0.9 mol of Dynasylan® TEOS and 0.15 g of Catalyst No. 1 (corresponding to 0.0154 mmol of Pt) were initially charged in a 0.5 l stirred apparatus with reflux condenser, metering apparatus. At a temperature of 131-161° C., a mixture consisting of 0.25 mol of TAICROS®, 4.83 mmol of benzoic acid and 26.08 mmol of ethanol was metered in within 1 hour. Thereafter, the mixture was left to react further at 157-162° C. for another 1 hour. Subsequently, 21.0 g of low boilers were removed at 78-128° C. and a pressure of <0.1 mbar. This gave 184.3 g of completely converted and colourless bottom product.

Evaluation of the $^1$H NMR Spectrum with Regard to Inventive Example 10:

| Solvent: CDCl$_3$ + 0.5% TMS | Signal at [ppm] | Integral | N Number of protons | I/N | % (mol) |
|---|---|---|---|---|---|
| S1 | 0.64 | 100.0 | 2 | 50.00 | 97.5 |
| A1 | 5.26 | 0.03 | 2 | 0.03 | <0.1 |
| P1 | 0.94 | 0.93 | 3 | 0.93 | 1.8 |
| I1 | 1.06 | 0.34 | 3 | 0.34 | 0.7 |

Result: 97.5% of the allyl groups were converted by hydrosilylation with TMOS to triethoxysilylalkyl groups (cf. S1). Allyl groups (A1) are still detectable only in very small amounts. 1.8% propyl groups (P1) and 0.7% isopropyl groups (I1) that contaminate the product were formed. The conversion of the allyl groups is complete, and only a low level of by-products is formed.

Example 11

3.75 mol of Dynasylan® TMOS and 0.3 g of "Karstedt catalyst" No. 2 (corresponding to 0.03845 mmol of Pt) were initially charged in a 1 l stirred apparatus with reflux condenser, metering apparatus. At a temperature of 74-79° C., a mixture consisting of 1.17 mol of TAICROS®, 22.93 mmol of benzoic acid and 121.87 mmol of methanol was metered in within 1 hour. Thereafter, the mixture was left to react further at 75-78° C. for about 1 further hour. Subsequently, 33.7 g of low boilers were removed at 100-129° C. and a pressure of <0.1 mbar. This gave 716.2 g of completely converted and colourless bottom product.

Evaluation of the $^1$H NMR Spectrum with Regard to Inventive Example 11:

| Solvent: CDCl$_3$ + 0.5% TMS | Signal at [ppm] | Integral | N Number of protons | I/N | % (mol) |
|---|---|---|---|---|---|
| S1 | 0.66 | 100.0 | 2 | 50.00 | 98.4 |
| A1 | 5.25 | 0.02 | 2 | 0.01 | <0.1 |
| P1 | 0.94 | 1.90 | 3 | 0.63 | 1.2 |
| I1 | 1.01 | 0.48 | 3 | 0.16 | 0.3 |

Result: 98.4% of the allyl groups were converted by hydrosilylation with TMOS to trimethoxysilylalkyl groups (cf. S1). Allyl groups (A1) are still detectable in very small amounts. 1.2% propyl groups (P1) and 0.3% isopropyl groups (I1) that contaminate the product were formed. The conversion of the allyl groups is complete, and only a low level of by-products is formed.

Example 12

1.2 mol of Dynasylan® TMOS and 0.16 g of Catalyst No. 4 (corresponding to 0.02050 mmol of Pt) were initially charged in a 0.5 l stirred apparatus with reflux condenser, metering apparatus. At a temperature of 73-84° C., a mixture consisting of 0.33 mol of TAICROS®, 6.55 mmol of benzoic acid and 34.38 mmol of methanol was metered in within 1¼ hour. Thereafter, the mixture was left to react further at 82-89° C. for about another ¾ hour. Subsequently, 23.1 g of low boilers were removed at 112-125° C. and a pressure of <0.1 mbar. This gave 204.8 g of completely converted and colourless bottom product.

Evaluation of the $^1$H NMR Spectrum with Regard to Inventive Example 12:

| Solvent: CDCl$_3$ + 0.5% TMS | Signal at [ppm] | Integral | N Number of protons | I/N | % (mol) |
|---|---|---|---|---|---|
| S1 | 0.66 | 100.0 | 2 | 50.00 | 98.5 |
| A1 | 5.25 | — | 2 | — | <0.1 |
| P1 | 0.94 | 1.90 | 3 | 0.63 | 1.2 |
| I1 | 1.01 | 0.46 | 3 | 0.30 | 0.3 |

Result: 98.5% of the allyl groups were converted by hydrosilylation with TMOS to trimethoxysilylalkyl groups (cf. S1). Allyl groups (A1) are no longer detectable. 1.2% propyl groups (P1) and 0.3% isopropyl groups (I1) that contaminate the product were formed. The conversion of the allyl groups is complete, and only a low level of by-products is formed.

Example 13

1.2 mol of Dynasylan® TMOS and 1.46 g of platinum-activated carbon (10% platinum on activated carbon, corresponding to 0.748 mmol of Pt) were initially charged in a 0.5 l stirred apparatus with reflux condenser, metering apparatus. At a temperature of 72-91° C., a mixture consisting of 0.33 mol of TAICROS®, 6.55 mmol of benzoic acid and 34.38 mmol of methanol was metered in within 1¼ hour. Thereafter, the mixture was left to react further at 80-89° C. for about another ¾ hour. Subsequently, the platinum catalyst was recovered via a pressure filtration, and 14.2 g of low boilers were removed at 95-138° C. and a pressure of <0.1 mbar. This gave 198.2 g of completely converted and colourless bottom product.

Evaluation of the $^1$H NMR Spectrum with Regard to Inventive Example 13:

| Solvent: CDCl$_3$ + 0.5% TMS | Signal at [ppm] | Integral | N Number of protons | I/N | % (mol) |
|---|---|---|---|---|---|
| S1 | 0.66 | 100.0 | 2 | 50.00 | 98.6 |
| A1 | 5.25 | — | 2 | — | <0.1 |
| P1 | 0.94 | 1.67 | 3 | 0.56 | 1.1 |
| I1 | 1.01 | 0.42 | 3 | 0.14 | 0.3 |

Result: 98.6% of the allyl groups were converted by hydrosilylation with TMOS to trimethoxysilylalkyl groups (cf. S1). Allyl groups (A1) are no longer detectable. 1.1% propyl groups (P1) and 0.3% isopropyl groups (I1) that contaminate the product were formed. The conversion of the allyl groups is complete, and only a low level of by-products is formed.

Example 14

1.2 mol of Dynasylan® TMOS and 0.2 g of Catalyst No. 1 (corresponding to 0.0205 mmol of Pt) were initially charged in a 0.5 l stirred apparatus with reflux condenser, metering apparatus. At a temperature of 71-96° C., a mixture consisting of 0.33 mol of TAICROS®, 6.55 mmol of benzoic acid and 34.38 mmol of benzyl alcohol was metered in within 1 hour. Thereafter, the mixture was left to react further at 83° C. for about 1 further hour. Subsequently, 21.4 g of low boilers were removed at 70-136° C. and a pressure of <0.1 mbar. This gave 207.2 g of completely converted and colourless bottom product.

Evaluation of the ¹H NMR Spectrum with Regard to Inventive Example 14:

| Solvent: CDCl$_3$ + 0.5% TMS | Signal at [ppm] | Integral | N Number of protons | I/N | % (mol) |
|---|---|---|---|---|---|
| S1 | 0.66 | 100.0 | 2 | 50.00 | 98.6 |
| A1 | 5.25 | 0.01 | 2 | <0.01 | <0.1 |
| P1 | 0.94 | 1.74 | 3 | 0.58 | 1.1 |
| I1 | 1.01 | 0.42 | 3 | 0.14 | 0.3 |

Result: 98.6% of the allyl groups were converted by hydrosilylation with TMOS to trimethoxysilylalkyl groups (cf. S1). Allyl groups (A1) are still detectable in very small amounts. 1.1% propyl groups (P1) and 0.3% isopropyl groups (I1) that contaminate the product were formed. The conversion of the allyl groups is complete, and only a low level of by-products is formed.

Example 15

1.2 mol of Dynasylan® TMOS and 0.2 g of catalyst (corresponding to 0.0205 mmol of Pt) were initially charged in a 0.5 l stirred apparatus with reflux condenser, metering apparatus. At a temperature of 72-90° C., a mixture consisting of 0.33 mol of TAICROS®, 6.55 mmol of benzoic acid and 34.38 mmol of diethylene glycol monomethyl ether was metered in within 1 hour. Thereafter, the mixture was left to react further at 84° C. for about 1 further hour. Subsequently, 22.4 g of low boilers were removed at 92-138° C. and a pressure of <0.1 mbar. This gave 208.7 g of completely converted and colourless bottom product.

Evaluation of the ¹H NMR Spectrum with Regard to Inventive Example 15:

| Solvent: CDCl$_3$ + 0.5% TMS | Signal at [ppm] | Integral | N Number of protons | I/N | % (mol) |
|---|---|---|---|---|---|
| S1 | 0.66 | 100.0 | 2 | 50.00 | 98.5 |
| A1 | 5.25 | 0.03 | 2 | 0.02 | <0.1 |
| P1 | 0.94 | 1.82 | 3 | 0.61 | 1.2 |
| I1 | 1.01 | 0.40 | 3 | 0.13 | 0.3 |

Result: 98.5% of the allyl groups were converted by hydrosilylation with TMOS to trimethoxysilylalkyl groups (S1). Allyl groups (A1) are still detectable in very small amounts. 1.2% propyl groups (P1) and 0.3% isopropyl groups (I1) that contaminate the product were formed. The conversion of the allyl groups is complete, and only a low level of by-products is formed.

European patent application 16180821.7 filed Jul. 22, 2016, is incorporated herein by reference.

Numerous modifications and variations on the present invention are possible in light of the above teachings. It is therefore to be understood that within the scope of the appended claims, the invention may be practiced otherwise than as specifically described herein.

The invention claimed is:

1. A process for preparing at least one tris[3-(alkoxysilyl)propyl] isocyanurate selected from the group consisting of tris[3-(trialkoxysilyl)propyl] isocyanurate, tris[3-(alkyldialkoxysilyl)propyl] isocyanurate and tris[3-(dialkylalkoxysilyl)propyl] isocyanurate by hydrosilylation, the process comprising:
 a) preparing a mixture of at least one hydroalkoxysilane (H-silane) selected from the group consisting of hydrotrialkoxysilane, hydroalkyldialkoxysilane, and hydrodialkylalkoxysilane, and a Pt catalyst;
 b) heating the mixture to a temperature of 40 to 170° C.;
 c) then adding or metering in an olefin component which is 1,3,5-triallyl-1,3,5-triazine-2,4,6(1H,3H,5H)-trione, at least one carboxylic acid and at least one alcohol as cocatalyst to the mixture while mixing the mixture; and
 d) leaving the mixture to react with the olefin component, the carboxylic acid, and the alcohol to produce a product mixture comprising the tris[3-(alkoxysilyl)propyl] isocyanurate.

2. The process according to claim 1, wherein a molar ratio of the H-silane to the alcohol is 1:0.01 to 0.2.

3. The process according to claim 1, wherein a molar ratio of the H-silane to the Pt catalyst is 1:1×10$^{-4}$ to 1×10$^{-9}$.

4. The process according to claim 1, wherein a molar ratio of the H-silane to the carboxylic acid is 1:1×10$^{-3}$ to 30×10$^{-3}$.

5. The process according to claim 1, wherein a molar ratio of the H-silane to the olefin component is 1:0.1 to 0.5.

6. The process according to claim 1, wherein the carboxylic acid is at least one selected from the group consisting of benzoic acid, propionic acid, 3,5-di-tert-butylbenzoic acid, 3,5-di-tert-butyl-4-hydroxybenzoic acid, and acetic acid.

7. The process according to claim 1, wherein the alcohol is a C1-C10 alcohol.

8. The process according to claim 1, wherein the H-silane is at least one selected from the group consisting of hydrotrimethoxysilane (TMOS), hydrotriethoxysilane (TEOS), methyldiethoxysilane (DEMS), methyldimethoxysilane (DMMS), dimethylethoxysilane (DMES), and dimethylmethoxysilane (MDMS).

9. The process according to claim 1, wherein the Pt catalyst is a Karstedt catalyst or is Pt applied to a solid catalyst support.

10. The process according to claim 1, further comprising:
 after the leaving in d), removing a heterogeneous catalyst, if any, from the product mixture; and then
 performing a distillative workup at 45-150° C. and a reduced pressure, to remove low boilers from the product mixture to obtain the tris[3-(alkoxysilyl)propyl] isocyanurate,
 wherein
 the H-silane and the Pt catalyst are initially charged and heated as a mixture,
 the olefin component, the carboxylic acid and the alcohol are combined and a cocatalyst mixture comprising the olefin component, the carboxylic acid and the alcohol is metered into the initial charge at a temperature in the initial charge of 40-135° C. while mixing over a period of time of 1 to 10 hours, and
 in the leaving in d), the mixture is left to react over a period of time of 0.5 to 2 hours.

11. The process according to claim 1,
 wherein a molar ratio of the H-silane to the alcohol is 1:0.01 to 0.2,
 a molar ratio of the H-silane to the Pt catalyst is 1:1×10$^{-4}$ to 1×10$^{-9}$,
 a molar ratio of the H-silane to the carboxylic acid is 1:1×10$^{-3}$ to 30×10$^{-3}$, and
 a molar ratio of the H-silane to the olefin component is 1:0.1 to 0.5.

12. The process according to claim 1,
 wherein a molar ratio of the H-silane to the alcohol is 1:0.02 to 0.2, a molar ratio of the H-silane to the Pt catalyst is $1:1\times10^{-4}$ to $9\times10^{-6}$, a molar ratio of the H-silane to the carboxylic acid is $2.7\times10^{-3}$ to $6\times10^{-3}$, and a molar ratio of the H-silane to the olefin component is 1:0.25 to 0.33.

13. The process according to claim 12, wherein the carboxylic acid is at least one selected from the group consisting of benzoic acid, propionic acid, 3,5-di-tert-butylbenzoic acid, 3,5-di-tert-butyl-4-hydroxybenzoic acid, and acetic acid, the H-silane is at least one selected from the group consisting of hydrotrimethoxysilane (TMOS), hydrotriethoxysilane (TEOS), methyldiethoxysilane (DEMS), methyldimethoxysilane (DMMS), dimethylethoxysilane (DMES), and dimethylmethoxysilane (MDMS), and the alcohol is at least one selected from the group consisting of tert-butanol, methanol, ethanol, benzyl alcohol, and diethylene glycol monomethyl ether.

14. The process according to claim 1, wherein the product mixture comprises 97.5 mol % or more of the tris[3-(alkoxysilyl)propyl] isocyanurate with respect to all compounds produced by hydrosilylation of the olefin component.

* * * * *